(12) United States Patent
Srinivasan (10) Patent No.: US 9,693,825 B2
(45) Date of Patent: *Jul. 4, 2017

(54) FIBER EMBEDDED HOLLOW NEEDLE FOR PERCUTANEOUS DELIVERY OF LASER ENERGY

(75) Inventor: Pattanam Srinivasan, Lebanon, IN (US)

(73) Assignee: C Laser, Inc., Lebanon, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/022,178

(22) Filed: Feb. 7, 2011

(65) Prior Publication Data
US 2011/0196357 A1    Aug. 11, 2011

Related U.S. Application Data

(63) Continuation-in-part of application No. 12/631,835, filed on Jan. 8, 2010, now Pat. No. 9,149,647.

(60) Provisional application No. 61/122,393, filed on Dec. 14, 2008.

(51) Int. Cl.
| | |
|---|---|
| *A61N 5/06* | (2006.01) |
| *A61B 18/20* | (2006.01) |
| *A61B 18/00* | (2006.01) |
| *A61B 18/22* | (2006.01) |

(52) U.S. Cl.
CPC .......... *A61B 18/201* (2013.01); *A61N 5/0601* (2013.01); *A61B 2018/00434* (2013.01); *A61B 2018/00577* (2013.01); *A61B 2018/2005* (2013.01); *A61B 2018/2227* (2013.01); *A61N 2005/063* (2013.01); *A61N 2005/0612* (2013.01); *A61N 2005/0662* (2013.01)

(58) Field of Classification Search
CPC ..................... A61N 5/0601; A61B 2018/2005
USPC ..................................... 606/2–19; 607/88–94
See application file for complete search history.

(56) References Cited

U.S. PATENT DOCUMENTS

| | | | | |
|---|---|---|---|---|
| 4,566,438 | A * | 1/1986 | Liese et al. | 600/176 |
| 4,959,063 | A * | 9/1990 | Kojima | 606/15 |
| 5,464,436 | A | 11/1995 | Smith | |
| 5,514,126 | A | 5/1996 | Prescott | |
| 5,772,597 | A * | 6/1998 | Goldberger et al. | 600/473 |
| 5,807,261 | A * | 9/1998 | Benaron et al. | 600/473 |
| 6,080,148 | A | 6/2000 | Damasco et al. | |
| 6,157,854 | A | 12/2000 | Haber | |
| 6,267,779 | B1 | 7/2001 | Gerdes | |

(Continued)

FOREIGN PATENT DOCUMENTS

| | | |
|---|---|---|
| DE | 44 29 192 | 2/1996 |
| DE | 200 03 349 | 6/2000 |

(Continued)

OTHER PUBLICATIONS

PCT International Preliminary Report on Patentability for Application No. PCT/US2011/064376 dated Aug. 13, 2013, 7 pages.

(Continued)

*Primary Examiner* — John R Downey
(74) *Attorney, Agent, or Firm* — Fish & Richardson P.C.

(57) ABSTRACT

An apparatus facilitating percutaneous delivery of laser energy includes: a hollow needle having a cutting edge at an insertion end thereof; and a laser fiber fixedly embedded within the hollow needle, the embedded laser fiber within the needle being permanently fixed within the hollow needle as one non detachable unit.

14 Claims, 7 Drawing Sheets

(56) References Cited

U.S. PATENT DOCUMENTS

| | | | |
|---|---|---|---|
| 6,519,485 | B2 | 2/2003 | Wiesmann et al. |
| 6,663,659 | B2 | 12/2003 | McDaniel |
| 6,921,413 | B2 | 7/2005 | Mahadevan-Jansen et al. |
| 6,942,658 | B1 | 9/2005 | Rizoiu et al. |
| 7,976,571 | B2 | 7/2011 | Neuberger |
| 2001/0056278 | A1 | 12/2001 | Nield et al. |
| 2002/0045922 | A1 | 4/2002 | Nield et al. |
| 2002/0182186 | A1* | 12/2002 | Loeb ............... C12N 5/0663 424/93.7 |
| 2003/0028147 | A1 | 2/2003 | Aves et al. |
| 2003/0120267 | A1 | 6/2003 | Kaufman et al. |
| 2003/0212388 | A1 | 11/2003 | Ronn |
| 2003/0225331 | A1 | 12/2003 | Diederich et al. |
| 2004/0014199 | A1 | 1/2004 | Streeter |
| 2004/0082942 | A1 | 4/2004 | Katzman |
| 2004/0111132 | A1 | 6/2004 | Shenderova |
| 2005/0049582 | A1 | 3/2005 | DeBenedictis et al. |
| 2005/0065577 | A1 | 3/2005 | McArthur et al. |
| 2005/0113658 | A1 | 5/2005 | Jacobson et al. |
| 2005/0182293 | A1 | 8/2005 | Katzman |
| 2005/0283148 | A1 | 12/2005 | Janssen et al. |
| 2006/0206172 | A1 | 9/2006 | DiMauro |
| 2007/0162093 | A1 | 7/2007 | Porter |
| 2007/0179485 | A1* | 8/2007 | Yeik et al. ............... 606/15 |
| 2007/0185367 | A1 | 8/2007 | Abdou |
| 2007/0213792 | A1 | 9/2007 | Yaroslavsky |
| 2008/0027520 | A1* | 1/2008 | Choi ............... A61B 17/1688 607/89 |
| 2008/0077198 | A1 | 3/2008 | Webb et al. |
| 2008/0091249 | A1 | 4/2008 | Wang |
| 2008/0125836 | A1 | 5/2008 | Streeter et al. |
| 2008/0140023 | A1 | 6/2008 | McMillan |
| 2008/0249517 | A1* | 10/2008 | Svanberg ............. G02B 6/3809 606/15 |
| 2009/0069673 | A1 | 3/2009 | Tapalian et al. |
| 2009/0125036 | A1 | 5/2009 | Bleich |
| 2009/0299349 | A1 | 12/2009 | Kubota et al. |
| 2010/0016783 | A1 | 1/2010 | Bourke et al. |
| 2011/0218524 | A1* | 9/2011 | Cattaneo ............... 606/12 |
| 2011/0301581 | A1 | 12/2011 | Thyzel |
| 2013/0281839 | A1 | 10/2013 | Jain et al. |
| 2016/0015997 | A1 | 1/2016 | Srinivasan |

FOREIGN PATENT DOCUMENTS

| | | |
|---|---|---|
| JP | 2009207605 A | 9/2009 |
| KR | 100 963 395 | 6/2010 |
| WO | WO 98/33557 | 8/1998 |
| WO | WO0057804 A1 | 10/2000 |
| WO | WO 01/62171 | 8/2001 |

OTHER PUBLICATIONS

PCT International Preliminary Report on Patentability for Application No. PCT/US2011/066006 dated Aug. 13, 2013, 7 pages.

Morgan & Mikhail, Clinical Anesthesiology, second edition, Chapter 18, Pain Management, pp. 274-280 (12 total pages).

Non-Final Office Action for U.S. Appl. No. 12/631,835 dated Dec. 20, 2011, 12 pages.

Final Office Action for U.S. Appl. No. 12/631,835 dated Mar. 14, 2013, 31 pages.

http://en.wikipedia.org/wiki/Local anesthetic.

Tsai et al.; Plasma-mediated ablation: an optical tool for submicrometer surgery on neuronal and vascular systems; Science Direct, Current Opinion in Biotechnology 2009, 20:1-10; www.sciencedirect.com.

Singh et al.; Percutaneous Lumbar Laser Disc Decompression: A Systematic Review of Current Evidence; Pain Physician 2009; 12:573-588 ISSN 1533-3159: www.painphysicianjournal.com.

Schenk et al.; Percutaneous Laser Disk Decompression: A Review of Literature; AJNR 27; Jan. 2006; www.ajnr.org.

Non-Final Office Action for U.S. Appl. No. 12/631,835 dated Sep. 4, 2012, 25 pages.

Final Office Action for U.S. Appl. No. 12/631,835 dated Jun. 19, 2012, 19 pages.

Non-Final Office Action for U.S. Appl. No. 13/329,596 dated Nov. 14, 2013, 16 pages.

Non-Final Office Action for U.S. Appl. No. 12/631,835 dated Mar. 14, 2014, 30 pages.

European Search Report issued in Application No. 11858224.6 on Feb. 27, 2015, 3 pages.

Final Office Action for U.S. Appl. No. 12/631,835 dated Jan. 12, 2015, 23 pages.

Notice of Allowance in U.S. Appl. No. 13/329,596, dated Dec. 24, 2014, 14 pages.

Communication Pursuant to Article 94(3) EPC issued in EP 11858224.6 on Mar. 19, 2015, 5 pages.

Turgut et al.; Extensive Damage to the End-Plates as a Complication of Laser Discectomy an Experimental Study Using an Animal Model; Acta Neurochirurgical 1997; 139: 404-410.

PCT Notification of Transmittal of the International Search Report and the Written Opinion of the International Searching Authority, or the Declaration issued in PCT/US2011/064376 on Feb. 6, 2012, 8 pages.

PCT Notification of Transmittal of the International Search Report and the Written Opinion of the International Searching Authority, or the Declaration issued in PCT/US2011/066006 on Apr. 19, 2012, 8 pages.

Non-Final Office Action for U.S. Appl. No. 12/631,835 dated Sep. 4, 2012, 26 pages.

European Office Action in Application No. 11858106.5, dated Sep. 2, 2014, 5 pages.

European Search Report in Application No. 11858106.5, dated Aug. 21, 2014, 3 pages.

Notice of Allowance in U.S. Appl. No. 12/631,835 , dated Jul. 9, 2015, 17 pages.

International Search Report and Written Opinion in International Application No. PCT/US2015/025870, mailed Jul. 24, 2015, 9 pages.

Communication Pursuant to Article 94(3) EPC issued in EP 11858106.5, dated Nov. 10, 2015, 3 pages.

Ren, Shiyan et al., "Retained Foeign Body After Laser Ablation", Int. Surg., Oct.-Dec. 2012; 97(4); 293-5.

International Preliminary Report on Patentability for PCT/US2015/025870, mailed Oct 27, 2016, 8 pages.

Non-Final Office action for U.S. Appl. No. 14/870,327, dated Oct. 6, 2016, 16 pages.

* cited by examiner

FIBER EMBEDDED HOLLOW NEEDLE FOR PERCUTANEOUS DELIVERY OF LASER ENERGY

CROSS-REFERENCE TO RELATED APPLICATIONS

This application is a Continuation-in-Part of U.S. application Ser. No. 12/631,835, filed Dec. 6, 2009, which claims benefit of U.S. Provisional Patent Application No. 61/122,393, filed Dec. 14, 2008, the entirety of each of which are incorporated by reference herein.

BACKGROUND OF THE INVENTION

The present invention relates to the delivery of laser energy to nerve endings to alleviate pain. The delivery of laser energy deep into the body for therapeutic use through the percutaneous method using an initial hollow probe or hollow needle placement is cumbersome.

BRIEF SUMMARY OF THE INVENTION

In accordance with an aspect of the present invention, an apparatus facilitating percutaneous delivery of laser energy includes: a hollow needle having a cutting edge at an insertion end thereof; and a laser fiber fixedly embedded within the hollow needle, the embedded laser fiber within the needle being permanently fixed within the hollow needle as one non detachable unit.

In another aspect, the laser fiber is embedded such that the laser fiber does not protrude past a point at which the cutting edge begins.

In another aspect, the cutting edge is a beveled edge.

In another aspect, the embedded laser fiber is permanently fixed within the hollow needle with glue.

In another aspect, the hollow needle has an outer diameter of 0.7 mm or less and is comparable to a spinal needle for maximal preservation and minimal disruption of the tissue integrity during insertion.

In another aspect, the laser fiber is precisely affixed within the hollow needle cavity so as the laser fiber tip does not protrude beyond the pointed tip of the hollow needle, thus preventing splitting and damage to the laser fiber while precisely delivering the laser energy on contact with the area of treatment.

In another aspect, the apparatus further comprises a laser generator that generates a laser of a wavelength in the 690 nm to 710 nm range.

In another aspect, the laser fiber has a diameter less than 0.7 mm.

In another aspect, the laser fiber has a diameter less than 0.5 mm.

In another aspect, the hollow needle is a Quincke type spinal needle.

In another aspect, the glue is a bioadhesive.

BRIEF DESCRIPTION OF THE DRAWINGS

The figures are for illustration purposes only and are not necessarily drawn to scale. The invention itself, however, may best be understood by reference to the detailed description which follows when taken in conjunction with the accompanying drawings in which.

DETAILED DESCRIPTION OF THE INVENTION

The present inventor has invented a delivery system and method described in co-pending U.S. application Ser. No. 12/631,835, filed Dec. 6, 2009: "Method for Deep Tissue Low intensity Therapy For Selective Destruction of Nociceptive (pain) Nerves," the entirety of which is incorporated herein by reference, which incorporates a spinal needle for laser delivery deep into the body. In this method, the laser fiber is fixed within the spinal needle as one unit to prevent movement, for example using a luer lock mechanism.

In particular, in deep tissue low intensity laser therapy (DT-LILT) a low intensity laser capable of producing cell resonance within the nerve cell can selectively cause destruction of the nerve cells without affecting the surrounding tissues. The selection of laser wavelength will depend on the absorption characteristics of the nerve cells. Heat may or may not be generated, and is not particularly necessary as the selective destruction of the nerve cells takes place by cell resonance rather than heat coagulation. This technique is referred to herein as deep tissue low intensity laser neuroablation (DT-LILNA) and is different from other medical or tissue lasers whose primary effect is through heat generation.

A delivery system for DT-LILT includes a laser generator capable of generating the appropriate wavelength. Desirable wavelengths are in the 690 nm to 710 nm range. Preferably the laser fibers used in the performing the process have diameters less than 0.7 and 0.5 mm.

The above described treatment preferably uses a common Quincke spinal needle with the laser fiber fixated in the needle. One way of fixating the laser fiber is by use of a luer lock mechanism with the Quincke needle. Such fixation can also be achieved by making the laser fiber and the spinal needle as one non detachable unit, as will be discussed in more detail below.

Preferred laser characteristics are as follows:
1. Laser Wavelength: 700 nm to 705 nm
2. Laser Output Average Power: 4 mW to 6 mW (range 1 mW to 6 mW)
3. Laser Pulsation, pulsed at nano seconds or picoseconds
4. Laser is Timer controlled: 5 s and 10 s.

Intra-operative Treatment Methodology:

The above technique can be applied to Facet Joint Neuroablation (also known as synonymous medial branch neuroablation). Conventional neuroablation is contingent upon finding the medial branch nerve in an oblique/lateral X ray view and using heat or chemical substance to destroy the medial branch. The method described here permits the use of a simple AP X-ray view and obtain correct positioning for deep tissue low intensity laser neuroablation.

The laser points for using DT-LILT by use of the present method is described next in the context of the lumbar facet joint. However, the use of the laser is not limited to these points, and these laser points are applicable to all facet joints, including thoracic and cervical facet joints. When the size of the facet joint is smaller, the laser points and the laser area reduce but the pattern of laser delivery remains the same.

Figure 1:
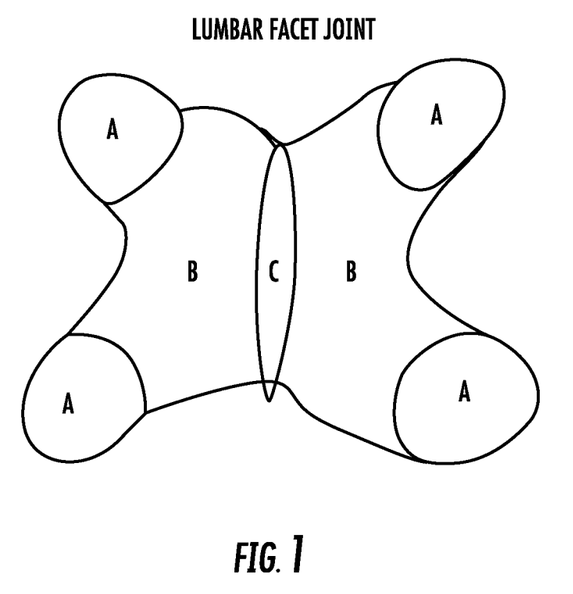
FIG. 1 is a diagram representative of an AP X-Ray view of Lumbar Facet Joints.

FIG. 1 is a diagram representative of an AP X-Ray view of Lumbar Facet Joints. As shown in FIG. 1, area A is the Facet Joint (also known as pars articularis), area B is the Lamina, and area C is the Spinous Process. The preferred laser points are next shown with reference to FIGS. 2-8.

Figure 2:
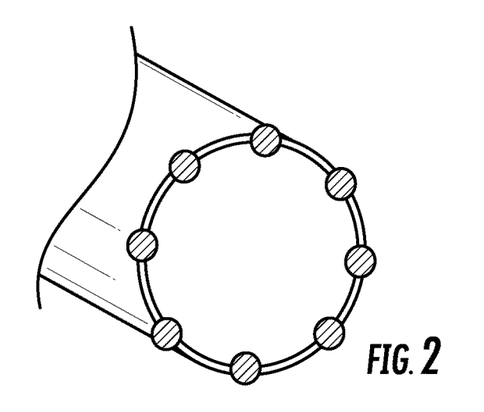
FIG. 2 is a diagram illustrating a technique in which the Laser points are used in a single lumbar facet using 8 points in a circular fashion around the facet joint.
Figure 3:
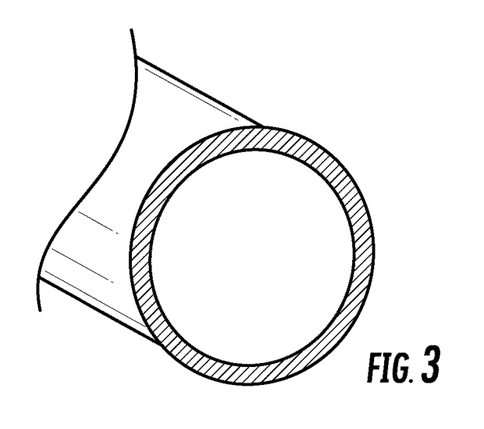
FIG. 3 is a diagram illustrating a technique in which the Laser points are applied in continuous circular fashion around the facet joint.
Figure 4:
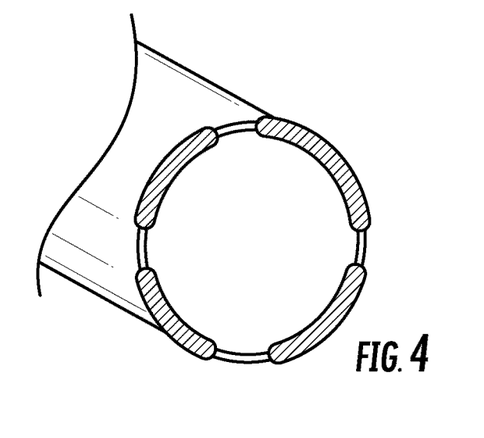
FIG. 4 is a diagram illustrating a technique in which the Laser points are applied in 4 semi continuous patterns around the facet joint.

FIG. 2 shows a technique in which the Laser points are used in a single lumbar facet using 8 points in a circular fashion around the facet joint. Another technique is illustrated in FIG. 3, in which the laser is applied in a continuous circular fashion around the facet joint. FIG. 4 illustrates a technique in which 4 semi continuous patterns are used around the facet joint.

Figure 5:
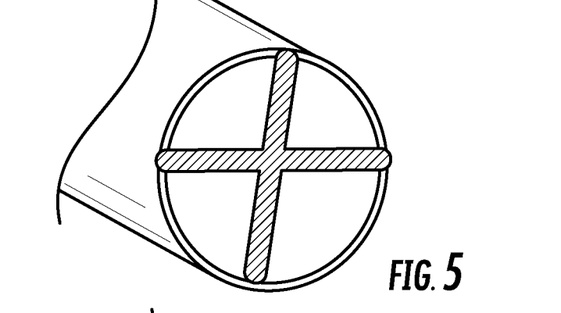
FIG. 5 is a diagram illustrating a technique in which the laser points on a single lumbar facet joint use a continuous cross pattern across the facet joint.
Figure 6:
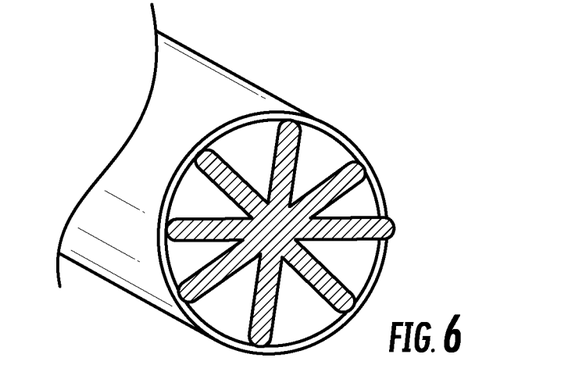
FIG. 6 is a diagram illustrating a technique in which the laser points on a single lumbar facet use continuous multiple cross patterns across the facet joint.
Figure 7:
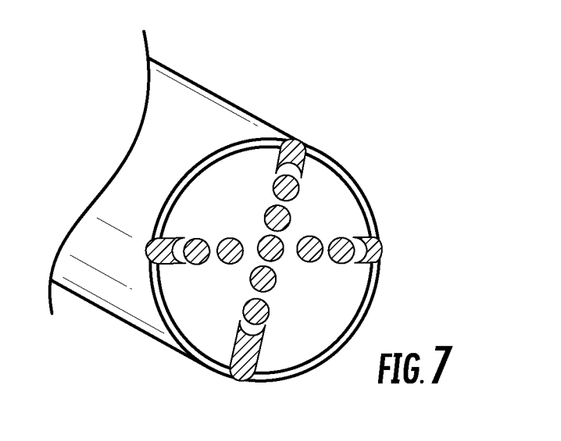
FIG. 7 is a diagram illustrating a technique in which the laser points on a single lumbar facet use a continuous intermittent pattern 4 across the facet joint.
Figure 8:
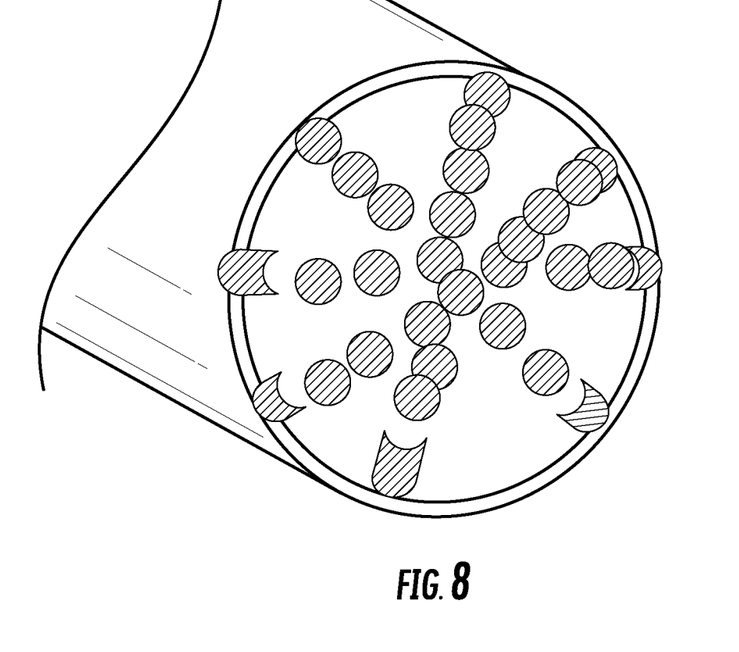
FIG. 8 is a diagram illustrating a technique in which the laser points on a single lumbar facet use a continuous intermittent pattern multiple times across the facet joint.

FIG. 5 shows the laser points on a single lumbar facet joint using another pattern: a continuous cross fashion across the facet joint. FIG. 6 shows the laser points using continuous multiple cross fashion across the facet joint, while FIG. 7 shows application of the laser in a continuous intermittent fashion 4 across the facet joint. FIG. 8 shows application of the laser in a continuous intermittent fashion multiple times across the facet joint.

The delivery of laser energy deep into the body for therapeutic use through the percutaneous method using an initial hollow probe or hollow needle placement is cumbersome. Moreover, even when the laser fiber is secured by use of a luer lock, the placement of the laser may not be secure.

When using a luer lock, the step of inserting the fiber within the spinal needle and affixing it with a luer lock mechanism may be prone to user errors, as careful visualization of the tip of the spinal needle is needed to prevent protrusion of the laser fiber beyond the needle tip. Such protrusion even if it is minimal can cause pain and discomfort in the patient during percutaneous insertion. Hollow or spinal needles inserted with protruded tips may also split or damage the laser fiber resulting in improper laser delivery to the area intended for treatment.

Also, first inserting the hollow probe or the hollow needle or a spinal needle and then inserting the laser fiber could result in migration of the laser fiber beyond the needle tip losing precision for the area of intended treatment as the needle tip is already embedded in the human body and is no longer under visual control. Such migration is contraindicated in spinal procedures where precision is required at all times. Repositioning the needle under these circumstances can also lead to unrecognized or unintended migration of the laser fiber. Furthermore migration of the laser fiber during laser delivery can irritate or even damage the healthy tissues that required no treatment in the first place.

As described above, deep tissue laser treatments may be facilitated using a hollow needle and a laser fiber that passes through that hollow needle. However free movement of the laser fiber within the hollow needle may not be safe and can result in the laser fiber getting in the way of needle movement. Free laser fiber movement within the hollow needle may also result in laser fiber damage by the needle tip resulting in improper and imprecise laser energy delivery within the human body. These problems can be eliminated by permanently embedding the laser fiber within the hollow needle and making the hollow needle and the laser fiber as one non detachable unit. Such an arrangement effectively prevents movement of the laser fiber within the hollow needle. The following describes in detail how the laser fiber may be embedded in a cutting edge hollow needle, such as a Quincke type spinal needle, so that the laser energy may be delivered in a safe and precise manner deep into the body.

Taking the above into consideration, an embodiment of the needle and fiber, in which the fiber is embedded in the hollow needle is described herein, in which the hollow needle and the laser fiber are formed as one non-detachable unit. This configuration offers excellent advantages and safety during delivery of laser energy over the previous hollow probe or hollow needle or spinal needle/laser fiber combinations. This technique, described in detail as follows, allows for easy insertion and precise delivery of laser energy to the area intended for treatment in a safe manner.

Figure 9:
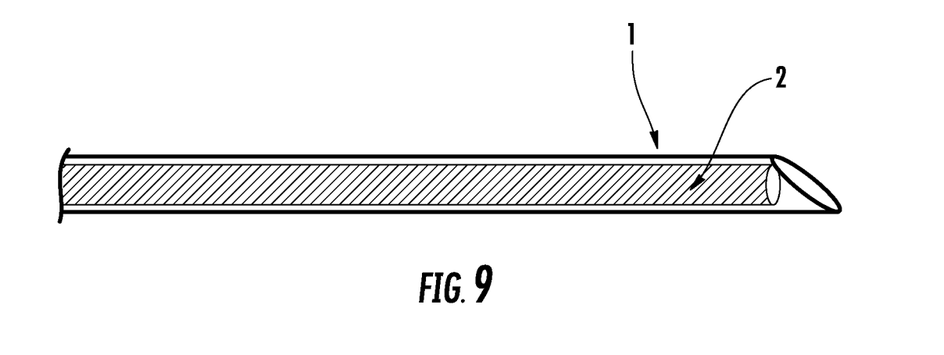
FIG. 9 a diagram that shows a hollow needle and permanently embedded laser fiber in accordance with an embodiment of the present application.
Figure 10:
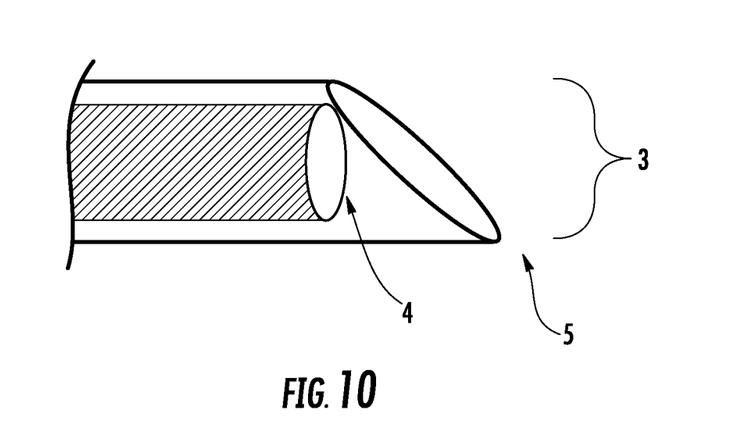
FIG. 10 is a diagram showing details of the tip of the hollow needle shown in FIG. 1.
Figure 11:
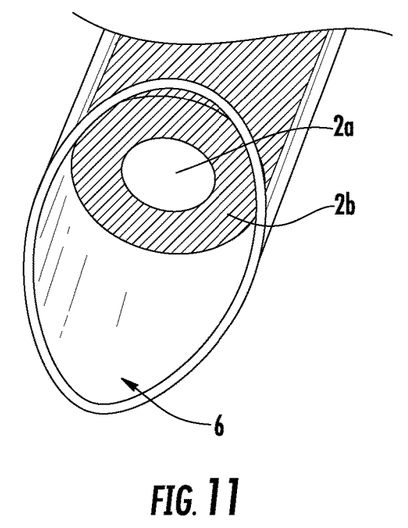
FIG. 11 is a view of the needle of FIGS. 9 and 10 shown from above.

A preferred embodiment of such a needle and laser fiber is shown in FIGS. 9-11. FIG. 9 shows the hollow needle 1 and the permanently embedded laser fiber 2 provided therein.

FIG. 10 shows the tip of the hollow needle along with the embedded laser fiber in magnification. The external diameter 3 of the hollow needle may vary from 0.7 mm or 22 G to 0.5 mm or 25 G. The tip of the needle 1 includes sharp edge of the bevel 5 that enables the hollow needle to pierce, and is characteristic of Quincke type spinal needles, also known as cutting edge spinal needles.

The tip of embedded laser fiber 4 is positioned to stop short of the tapering cutting edge of the hollow needle, as shown. In FIG. 11, the hollow needle is viewed from above. In this view it can be seen that the tip of the embedded laser fiber 2 is clear of the tapering cutting edge, leaving a triangular space 6 between the cutting edge of the hollow needle 1 and the tip of the embedded laser fiber 2. To maintain the fiber 2 in this preferred condition, the fiber 2 is affixed permanently within the hollow needle 1. 2a is the cavity of the fiber through which the laser is delivered, 2b is the laser fiber. The laser fiber is fixed to the inner wall of the Quincke spinal needle with a bio-adhesive to prevent movement. Preferably, permanent affixation of the laser fiber or embedding the laser fiber within the hollow needle precisely as shown in FIGS. 9-11 may be achieved using industrial standard bioadhesives, many types of which are available for, e.g., the DYMAX 136-M which is used in the manufacture of medical devices.

Figure 12:
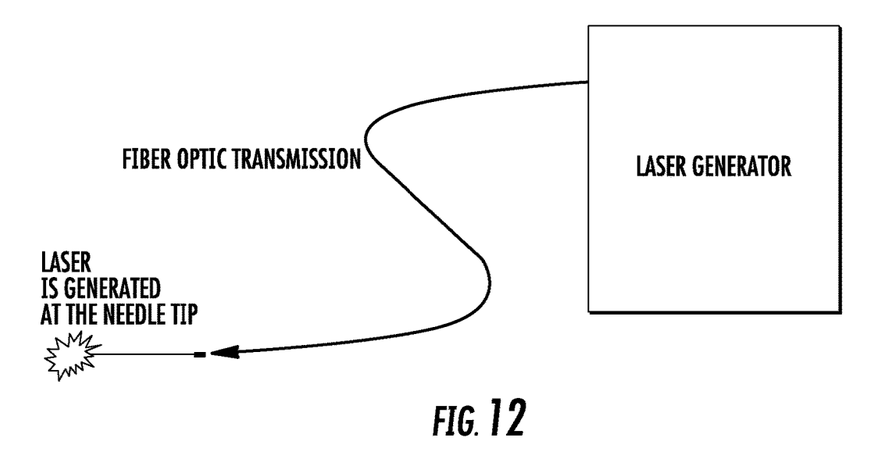
FIG. 12 is a schematic diagram of an apparatus for delivery of laser energy using the needle shown in FIGS. 9-11.

In FIG. 12, the schematic presentation of the delivery system for use with the needle as discussed above is shown. The delivery system is the same as the one described in "Method for Deep Tissue Low intensity Therapy For Selective Destruction of Nociceptive (pain) Nerves", except that the presentation in FIG. 12 has no luer lock mechanism and the fiberoptic transmission is present at one continuous unit along with the needle, the tip of which represents the point of final laser delivery.

Figure 13:
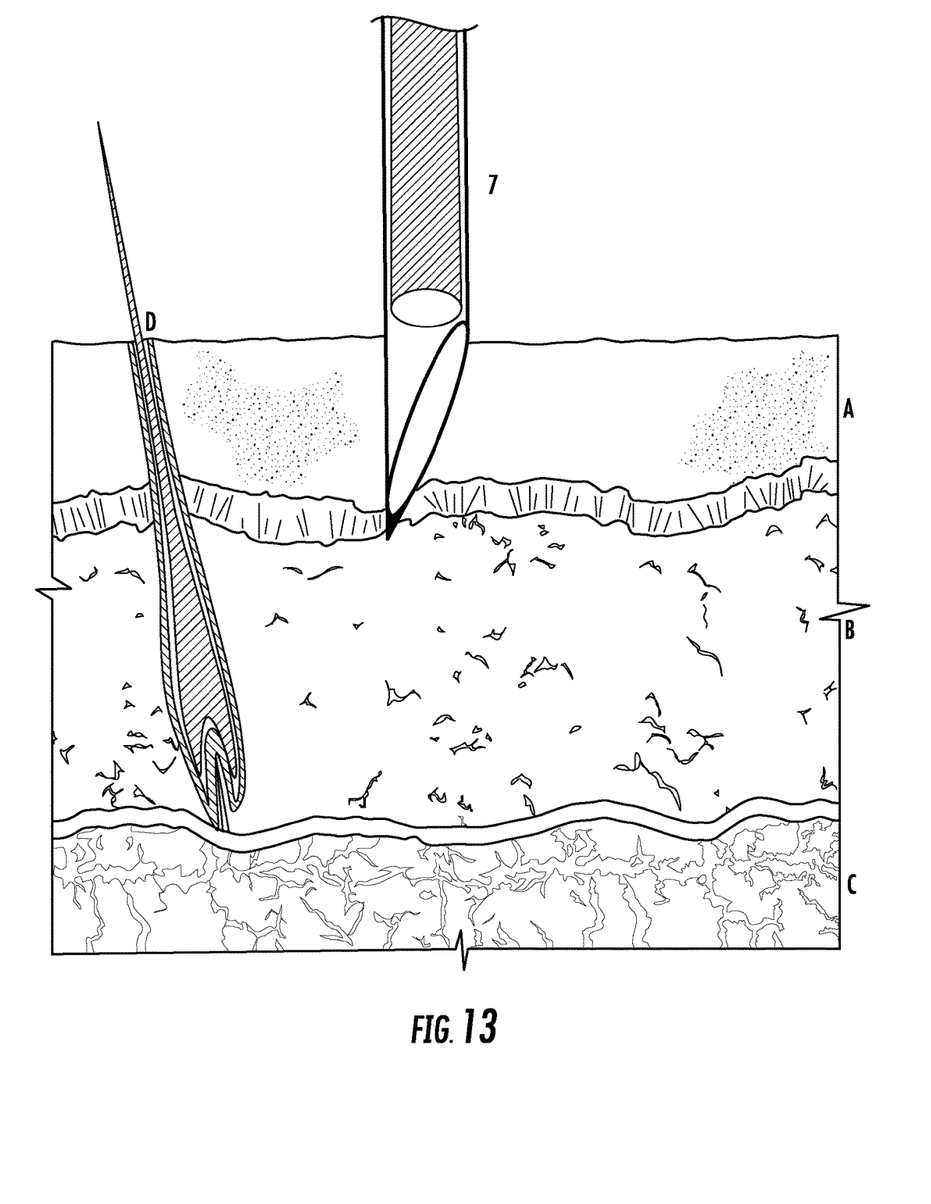
FIG. 13 is a diagram showing the needle in accordance with embodiments of the present invention entering the skin during use.

FIG. 13 represents the laser fiber embedded hollow needle 7 as it penetrates the skin which is represented schematically in cross section (A is epidermis, B is dermis, C is adipose tissue and D is hair arising from a hair follicle). The advantages of the disclosed embodiment is well demonstrated in this figure. As can be seen from the figure, the sharp edge or the cutting edge of the needle penetrates the skin easily, while the fiber embedded beyond the cutting edge is clear of the cutting edge and freely passes through the skin without obstructing penetration.

The above-described apparatus facilitates the precise and safe delivery of laser energy at the area of treatment percutaneously, while deeper application is also facilitated by advancing the needle as far as it is needed. As indicated in "Method for Deep Tissue Low intensity Therapy For Selective Destruction of Nociceptive (pain) Nerves" use of this laser embedded needle is facilitated by clinical diagnoses and with the help of image guidance such as X-rays to precisely place the needle at the area of treatment.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. An apparatus comprising:
   a hollow needle having a central cavity and a beveled cutting edge at the distal insertion end thereof; and
   a tubular laser fiber that is inserted into the central cavity of the hollow needle,
      wherein the tubular laser fiber is coaxial with an axis of the central cavity and is positioned such that a distal end of the tubular laser fiber is retracted within the central cavity corresponding to a plane defining a beginning of the beveled cutting edge, such that the tubular laser fiber is fully enveloped by an inner wall of the hollow needle surrounding the central cavity,
      wherein the tubular laser fiber is directly affixed to the inner wall of the hollow needle whereby the tubular laser fiber and the hollow needle become one non-detachable unit,
      whereby the apparatus in the above configuration facilitates unobstructed entry of the apparatus through skin and deeper structures of a human body without the requirement of additional elements, and
      wherein the hollow needle is a Quincke-type spinal needle.

2. The apparatus according to claim 1, wherein the laser fiber is non-detachably affixed to the inner wall of the hollow needle with a bioadhesive.

3. The apparatus according to claim 1, wherein the hollow needle has an outer diameter of 0.7 mm or less.

4. The apparatus according to claim 1, wherein the apparatus is coupled to a laser generator that transmits laser energy of a wavelength between 600 nm and 710 nm, and wherein the laser energy is conducted through the laser fiber.

5. The apparatus according to claim 3, wherein the laser fiber has a diameter of 0.5 mm or less.

6. The apparatus according to claim 1, wherein the laser fiber is positioned inside the central cavity of the hollow needle such that a tip of the laser fiber terminates at a plane corresponding to the beveled cutting edge of the hollow needle.

7. The apparatus according to claim 1, wherein the beveled cutting edge of the hollow needle is configured for penetrating skin, and wherein the laser fiber is positioned to terminate before the beveled cutting edge such that obstruction of the hollow needle from penetrating the skin is avoided.

8. The apparatus according to claim 1, wherein the apparatus is configured for insertion of a single laser fiber into the central cavity of the hollow needle.

9. The apparatus according to claim 1, wherein the hollow needle has an external diameter that varies in range between 0.7 mm or 22G and 0.5 mm or 25G.

10. The apparatus according to claim 1, wherein the laser fiber has a diameter of 0.7 mm or less.

11. The apparatus according to claim 2, wherein the bioadhesive includes an industrial standard bioadhesive.

12. The apparatus according to claim 4, wherein the laser energy is delivered to a treatment point through a tip of the laser fiber.

13. The apparatus according to claim 1, wherein the hollow needle includes a single central cavity that is configured to hold a laser fiber.

14. The apparatus according to claim 1, wherein the apparatus provides laser energy treatment to deeper structures of the human body while preventing damage to the deeper structures from laser fiber migration and damage to the laser fiber itself.

* * * * *

UNITED STATES PATENT AND TRADEMARK OFFICE
CERTIFICATE OF CORRECTION

PATENT NO. : 9,693,825 B2  
APPLICATION NO. : 13/022178  
DATED : July 4, 2017  
INVENTOR(S) : Pattanam Srinivasan

Page 1 of 1

It is certified that error appears in the above-identified patent and that said Letters Patent is hereby corrected as shown below:

In the Specification

Column 1, Line 9, please delete "Dec. 6, 2009", and insert therefor -- Jan. 8, 2010 --.

Signed and Sealed this
Twenty-second Day of August, 2017

Joseph Matal
*Performing the Functions and Duties of the*
*Under Secretary of Commerce for Intellectual Property and*
*Director of the United States Patent and Trademark Office*